United States Patent [19]

Hill et al.

[11] Patent Number: 5,698,684
[45] Date of Patent: Dec. 16, 1997

[54] PROCESS FOR THE PRODUCTION OF ALKYL GLYCOSIDES

[75] Inventors: Karlheinz Hill, Erkrath; Manfred Weuthen, Moenchengladbach; Hans-Peter Koehler, Duesseldorf, all of Germany

[73] Assignee: Henkel Kommanditgesellschaft auf Aktien, Duesseldorf, Germany

[21] Appl. No.: 835,447
[22] PCT Filed: Aug. 16, 1990
[86] PCT No.: PCT/EP90/01349
   § 371 Date: Feb. 24, 1992
   § 102(e) Date: Feb. 24, 1992
[87] PCT Pub. No.: WO91/02742
   PCT Pub. Date: Mar. 7, 1991

[30] Foreign Application Priority Data

Aug. 24, 1989 [DE] Germany .................. 39 27 919.7

[51] Int. Cl.$^6$ .................. C07G 3/00; C07H 15/04; B01J 31/00
[52] U.S. Cl. .................. 536/18.6; 536/18.5; 536/120; 502/168
[58] Field of Search .................. 536/18.6, 18.5, 536/120; 502/168

[56] References Cited

U.S. PATENT DOCUMENTS

| | | | |
|---|---|---|---|
| 3,598,865 | 8/1971 | Lew | 536/18.6 |
| 4,713,447 | 12/1987 | Letton | 536/18.6 |
| 5,003,057 | 3/1991 | McCurry et al. | 536/18.6 |

FOREIGN PATENT DOCUMENTS

| | | |
|---|---|---|
| 132043 | 1/1985 | European Pat. Off. . |
| 1905523 | 9/1969 | Germany . |

OTHER PUBLICATIONS

Chemical Abstracts, vol. 91, No. 19, issued 5 Nov. 1979, Hagiwara et al, "Alkylphenols" see p. 612, column 1, Abstract No. 157440v, Jpn. Kokai Tokkyo Koho 79/84,537 (cl. C07C 39/06), 5 Jul. 1979, Appl. 77/152,243, 16 Dec. 1977.

*Primary Examiner*—John Kight
*Assistant Examiner*—Everett White
*Attorney, Agent, or Firm*—Ernest G. Szoke; Wayne C. Jaeschke; Daniel S. Ortiz

[57] ABSTRACT

In the acid-catalyzed production of alkyl glycosides, the molar quantity of catalyst used can be clearly reduced in all processes of industrial interest by using sulfosuccinic acid as catalyst as opposed to conventional catalysts, such as sulfuric acid or p-toluene sulfonic acid. The end reaction products are lighter in color and less clouded than alkyl glycosides obtained with conventional catalysts. Sulfosuccinic acid is readily biodegradable.

20 Claims, No Drawings

PROCESS FOR THE PRODUCTION OF ALKYL GLYCOSIDES

This invention relates to a new improved process for the production of $C_{1-30}$ alkyl glycosides using an acid as catalyst.

Processes for the production of alkyl glycosides using a catalyst have been known for more than 50 years. Thus, Austrian patent 135 333 describes the production of lauryl glucoside and cetyl glucoside from acetobromoglucose and the appropriate fatty alcohol in the presence of a base. The direct synthesis from glucose and lauryl alcohol using hydrogen chloride as acidic catalyst is also described therein.

U.S. Pat. No. 3,547,828 describes a process from the production of surface-active alkyl glycosides, in which a saccharide is initially reacted with a lower alcohol, such as butanol, in the presence of an acidic catalyst to form a lower alkyl glycoside which then reacts with a higher alcohol to form the higher surface-active alkyl glycoside (transacetalization). Suitable acidic catalysts are mineral acids, such as sulfuric acid, hydrochloric acid and nitric acid, p-toluenesulfonic acid and methanesulfonic acid.

According to the reaching of U.S. Pat. No. 3,598,865, $C_{8-25}$ alkyl glycosides are prepared by the acid-catalyzed reaction of monosaccharide or oligo- or polysaccharide hydrolyzable to monosaccharide with a $C_{8-25}$ alcohol in the presence of a lower alcohol. The acidic catalyst is sulfuric acid, hydrochloric acid, phosphoric acid, phosphorous acid, toluenesulfonic acid or boron trifluoride.

U.S. Pat. No. 3,839,318 describes a process for the production of alkyl glycosides by direct acid-catalyzed reaction of a higher alcohol with a saccharide. Mineral acids, such as sulfuric acid and hydrochloric acid, and sulfoacid ion exchanger resins are mentioned as suitable catalysts.

According to European patent application 132 043, the acid form of an anionic surfactant, such as alkyl hydrogen sulfate, alkyl sulfonic acid and alkyl benzenesulfonic acid, is used as acidic catalyst in the production of alkyl glycosides obtained by reaction of a glycose unit with an alcohol (direct synthesis).

The problem addressed by the present invention is to extend the catalytst potential to the production of alkyl glycosides.

The present invention relates to a process for the production of alkyl glycosides corresponding to the general formula $RO(G)_n$, where G is a glycose unit, n is a number of 1 to 10 and R is an aliphatic $C_{1-30}$ radical, using sulfosuccinic acid as catalyst.

The alkyl glycosides obtainable in accordance with the invention using sulfosuccinic acid as catalyst may be represented by the general formula $RO(G)_n$. In this formula, the aliphatic radical R is derived from a $C_{1-30}$ alcohol. The higher aliphatic alcohols are preferably obtained by reduction of natural fats, so that in the context of the present disclosure the term alkyl in alkyl glycoside encompasses saturated and ethylenically unsaturated radicals and mixtures thereof, including those of different chain length in admixture with one another. Preferred aliphatic radicals are alkyl radicals of linear and primary $C_{8-22}$ and, more particularly, $C_{12-18}$ alcohols. Sulfosuccinic acid is also suitable for the production of alkyl glycosides of which the alkyl radical is derived form synthetic primary alcohols, more particularly from so-called oxoalcohols which are obtained by oxosynthesis or hydroformylation and which have a certain percentage content, generally 20 to 40%, of branched isomers with a 2-methyl radical. Typical alkyl glycosides which may be produced by the process according to the invention are those in which alkyl consists of octyl, nonyl, decyl, undecyl, dodecyl, 2-methyl undecyl, tridecyl, tetradecyl, pentadecyl, hexadecyl, heptadecyl, octadecyl and mixtures thereof.

The glycose unit G emanates from the usual aldoses or ketoses, such as for example glucose, fructose, mannose, glactose, arabinose and ribose, or from oligo- and polysaccharides which may be degraded to monosaccharides by hydrolysis. Among the monosaccharides, the aldoses and, more particularly, glucose are preferably used because they are easy to obtain and are available in commercial quantities. Commercial glucose frequently contains 1 mol water of crystallization. Where sulfosuccinic acid is used as catalyst in the production of alkyl glycosides, both anhydrous glucose and glucose containing water of crystallization may be used with equal effect. The most important polysaccharide degradable to a glucose unit is starch. Powder-form starches and their partial degradation products, for example in the form of a corresponding glucose syrup of generally high concentration, are also preferred starting materials.

The index n is a number of 1 to 10 and indicates the degree of oligomerization, i.e. the distribution of monoglycosides and oligoglycosides. Whereas, in a given compound, n must always be an integer and, above all, may assume a value of 1 to 6, the value n for a special product is an analytically determined mathematical quantity which generally represents a broken number.

Sulfosuccinic acid may be used as catalyst in any processes, particularly in any processes of industrial interest, for the acid-catalyzed production of alkyl glycosides. Thus, it may be used in processes where alkyl glycosides are obtained either by direct reaction of a monosaccharide, more particularly glucose, with an excess of aliphatic alcohol (direct synthesis) or where alkyl glycosides are obtained by reaction of a monosaccharide, particularly glucose, or an oligo- or polysaccharide degradable to a monosaccharide, more particularly starch or partial starch degradation products, with a lower preferably $C_{1-4}$ alcohol or glycol to form a lower alcohol glycoside which then reacts with a higher, preferably $C_{8-22}$ aliphatic alcohol to form a higher surface-active alkyl glycoside (transacetalization).

Through the use of sulfosuccinic acid as catalyst, the velocity of the reaction between mono-, oligo- or polysaccharide on the one hand and alcohol, more particularly aliphatic alcohol, on the other hand (direct synthesis and first step of the transacetalization process) and also the velocity of the reaction of the lower alkyl glycoside with the higher aliphatic alcohol (second step of the transacetalization process) are increased to a greater extent than by the use of the same molar quantities of conventional known catalysts, such as mineral acids, for example sulfuric acid, or p-toluenesulfonic acid. Through the use of sulfosuccinic acid, the reaction time can be shortened by 40 to 60% compared with the same molar quantities of conventional known catalysts.

Another major advantage of using sulfosuccinic acid as catalyst in the production of alkyl glycosides is that, for the same reaction time and/or for a predetermined conversion, the molar quantity of catalyst used per mol glycose unit can be reduced by at least 40%, preferably by up to 60% and, more preferably, by up to 80% compared with conventional catalysts, such as for example sulfuric acid and p-toluenesulfonic acid. Both in the direct synthesis and in the transacetalization process and, above all, in the transacetalization process starting from starch or partial starch degradation products, the sulfosuccinic acid is preferably used in quantities of 1 to 6 mmol per mol glycose unit, more preferably in quantities of 1.5 to 5 mmol and, most preferably, in quantities of 2.5 to 3.5 mmol per mol glycose unit.

The sulfosuccinic acid may be used in anhydrous from or in the form of an aqueous solution, more particularly in the form of a 60 to 80% by weight clear aqueous solution.

Other major advantages of sulfosuccinic acid lie in its ecological properties. Sulfosuccinic acid is not aromatic and is readily biodegradable.

The alkyl glycosides produced in accordance with the invention using sulfosuccinic acid as catalyst have the advantage that they are lighter in color and less clouded than alkyl glycosides produced using conventional catalysts. Another advantage is that, where relatively small quantities of catalyst are used in the neutralization step typically present in all production processes of commercial interest, it is sufficient to use correspondingly less neutralizing agent. The end products of the reaction thus have a lower salt content that products produced with the conventional catalysts typically used.

EXAMPLES

EXAMPLE 1

This Example describes the preparation of a $C_{12-14}$ alkyl glucoside from anhydrous glucose and a technical fatty alcohol (mixture of approx. 75% by weight dodecanol and approx. 25% by weight tetradecanol) in a molar ratio of 1:4.5 by the direct synthesis method.

5.6 mmol sulfosuccinic acid, corresponding to 1.6 g of a 70% solution in water, dissolved in 35 g (0.18 mol) of a dodecanol/tetradecanol mixture (Lorol S®, Henkel KGaA) were added in vacuo (20 mm Hg column) to a mixture heated to 115° C. of 838 g (4.32 mol) Lorol S® and 180 g (1 mol) anhydrous glucose (Puridex®, Cerestar Deutschland GmbH). The water formed as the reaction progressed was removed in vacuo, condensed by cooling with liquid nitrogen and quantitatively determined at intervals of 15 minutes. These values were corrected by 0.5 ml water brought in by the aqueous sulfosuccinic acid solution. The reaction conversion as a function of time was calculated therefrom (18 ml corresponded to a conversion of 100%). The values determined are shown in Table 1.

For comparison, the test was repeated with 5.6 mmol p-toluenesulfonic acid monohydrate (1.1 g) as catalyst. The reaction conversion determined as a function of time is also shown in Table 1.

TABLE 1

| Catalyst | Conversion after minutes | | | | | | |
|---|---|---|---|---|---|---|---|
| | 15 | 30 | 45 | 60 | 75 | 90 | 120 |
| Sulfosuccinic acid | 55% | 80% | 94% | 100% | 100% | 100% | 100% |
| p-Toluenesulfonic acid | 16% | 58% | 77% | 91% | 97% | 99% | 100% |

EXAMPLE 2

This Example describes the preparation of a $C_{12-14}$ alkyl glucoside by direct synthesis using glucose monohydrate.

Example 1 was repeated with 198 g (1 mol) glucose monohydrate which was suspended in Lorol S and dehydrated for 30 minutes at 80° C./15 mm Hg column. The conversions determined corresponded to those of Example 1.

EXAMPLE 3

Example 1 was repeated using 2.8 mmol sulfosuccinic acid as catalyst. The reaction was terminated after 2 hours as in the comparison test using 5.6 mmol p-toluene-sulfonic acid (see Table 1).

EXAMPLE 4

This Example describes the production of a $C_{12-14}$ alkyl glucoside by the transacetalization method starting form starch and a technical fatty alcohol in a molar ratio of 1:4.5. 190.6 g (1 mol) potato starch (water content (15%) were heated with stirring to 140° C. under a pressure of 6 bar with 593 g (8 mol) butanol, 79.4 g (4.4 mol) water and 0.8 g (2.8 mmol) 70% aqueous sulfosuccinic acid. After 30 minutes, the reaction mixture was cooled to 100° C. and the water was distilled off under normal pressure. 873 g (4.5 mol) Lorol S ($C_{12-14}$ fatty alcohol) were then added and the reaction mixture was heated to 110° C. Butanol distilled off in vacuo (20 mm Hg column) at that temperature. The distillation of butanol was terminated after 2 hours.

For comparison, the test was repeated with p-toluenesulfonic acid monohydrate as catalyst. 3.2 g (16.4 mmol) p-toluenesulfonic acid monohydrate had to be used to keep to the same reaction time (2 hours). After the removal of butanol by distillation, the product was distinctly darker in color than the product obtained with sulfosuccinic acid.

EXAMPLE 5

Example 3 was repeated with 593 g (8 mol) butanol.

EXAMPLE 6

Example 3 was repeated with 833.5 g (4.5 mol) of a dodecanol/tridecanol mixture (Neodol 23®, Shell).

EXAMPLE 7

Example 1 was repeated with 1091 g (4.5 mol) hexadecanol (Lorol $C_{16}$®, Henkel KGaA) and 4.2 mmol catalyst (sulfosuccinic acid or p-toluenesulfonic acid monohydrate).

The conversions determined in Examples 5 to 7 corresponded to those of Examples 1 to 3. In all the tests, the effect of the sulfosuccinic acid as catalyst was significantly stronger than that of p-toluenesulfonic acid.

We claim:

1. In a process for the manufacture of alkyl glycosides of the formula $RO(G)_n$, where G is a glycose unit, n is a number of from 1 to 10 and R is an aliphatic residue having 1–30 carbon atoms, by reaction of an aliphatic alcohol having from 1 to 30 carbon atoms with at least one member selected for the group consisting of reducing monosaccharide, oligosaccharides hydrolyzable to reducing monosaccharides and polysaccharides hydrolyzable to reducing monosaccharides in the presence of an acid catalyst the improvement which comprises: introducing sulfosuccinic acid into the process as the catalyst.

2. A process of claim 1, wherein the alkyl glycosides are prepared by reaction of a saccharide with a saturated linear, primary $C_{8-22}$ alcohol.

3. A process of claim 2 wherein sulfosuccinic acid is introduced into the process as a 60 to 80% by weight clear aqueous solution.

4. A process of claim 2 wherein the alcohol comprises a $C_{12}$ to $C_{18}$ linear, primary alcohol.

5. A process of claim 4 wherein 2.5 to 3.5 mmol of sulfosuccinic acid is introduced per mol of glycose unit.

6. A process of claim 2 wherein 1.5 to 5 mmol of sulfosuccinic acid is used per mol of glycose unit.

7. A process of claim 1 wherein 1.5 to 5 mmol of sulfosuccinic acid is introduced per mol glycose unit.

8. A process of claim 7 wherein sulfosuccinic acid is introduced into the process as a 60 to 80% by weight clear aqueous solution.

9. A process of claim 7 wherein 2.5 to 3.5 mmol of sulfosuccinic acid is introduced per mol of glycose unit.

10. A process of claim 1 wherein sulfosuccinic acid is introduced into the process as a 60 to 80% by weight clear aqueous solution.

11. In a process for the manufacture of alkyl glycosides of the formula $RO(G)_n$ where G is a glycose unit, n is a number of from 1 to 10 and R is an aliphatic residue having 2–30 carbon atoms by transacetylization of an alkyl glycoside of the formula $R^1O(G)_n$ wherein $R^1$ is an aliphatic residue having a lower number of carbon atoms than R, by reaction of an alcohol ROH with an alkyl glycoside of the formula $R^1O(G)_n$ in the presence of an acid catalyst the improvement which comprises: introducing sulfosuccinic acid into the process as the acid catalyst.

12. A process of claim 11 wherein ROH comprises a saturated, linear primary alcohol having from 8–22 carbon atoms.

13. A process of claim 12 wherein ROH comprises a saturated, linear, primary alcohol having from 12 to 18 carbon atoms.

14. A process of claim 13 wherein the sulfosuccinic acid is introduced into the process as a 60% to 80% by weight aqueous solution.

15. A process of claim 12 wherein the sulfosuccinic acid is introduced into the process as a 60% to 80% by weight aqueous solution.

16. A process of claim 11 wherein 1.5 to 5 mmol of sulfosuccinic acid is introduced per mol of glycose unit.

17. A process of claim 16 wherein the sulfosuccinic acid is introduced into the process as a 60% to 80% by weight aqueous solution.

18. A process of claim 11 wherein 2.5 to 3.5 mmol of sulfosuccinic acid is introduced per mol of glycose unit.

19. A process of claim 18 wherein the sulfosuccinic acid is introduced into the process as a 60% to 80% by weight aqueous solution.

20. A process of claim 11 wherein the sulfosuccinic acid is introduced into the process as a 60% to 80% by weight aqueous solution.

* * * * *